(12) United States Patent
Seth

(10) Patent No.: US 6,350,471 B1
(45) Date of Patent: *Feb. 26, 2002

(54) TABLET COMPRISING A DELAYED RELEASE COATING

(75) Inventor: Pawan Seth, Irvine, CA (US)

(73) Assignee: Pharma Pass LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/584,386

(22) Filed: May 31, 2000

(51) Int. Cl.⁷ .............................. A61K 9/32; A61K 9/36
(52) U.S. Cl. ...................... 424/480; 424/468; 424/482; 514/772.3; 514/781; 514/770; 514/772.2; 514/777; 514/784
(58) Field of Search .................................. 424/468, 474, 424/475, 480, 482, 476, 494, 495, 498, 497

(56) References Cited

U.S. PATENT DOCUMENTS 6,096,341 A * 8/2000 Seth ........................... 424/482

* cited by examiner

Primary Examiner—James M. Spear
(74) Attorney, Agent, or Firm—Alston & Bird LLP

(57) ABSTRACT

The invention provides a delayed release tablet, comprising: (i) a core comprising an active ingredient selected from the group consisting of oxybutynin hydrochloride, propranolol hydrochloride, buspiron hydrochloride, niacin, cetirizin hydrochloride, cerivastin sodium, metoprolol fumarate, and alendronate sodium., and conventional excipients; and (ii) a coating consisting essentially of a water-insoluble, water-permeable film- forming polymer, a plasticizer and a water-soluble polymer.

13 Claims, No Drawings

TABLET COMPRISING A DELAYED RELEASE COATING

BACKGROUND OF THE INVENTION

Numerous drugs require a delayed release dosage form. However, current technology for manufacturing such dosage forms usually involves matrix technology or the use of pore-forming agents. In some instances, these routes cannot be followed.

There is a need to obtain new release dosage form, which can be applied to numerous drugs, especially oxybutynin hydrochloride, propranolol hydrochloride, buspiron hydrochloride, niacin, cetirizin hydrochloride, cerivastin sodium, metoprolol fumarate, and alendronate sodium.

SUMMARY OF THE INVENTION

The invention provides a controlled release tablet comprising:

(i) a core comprising the active ingredient and conventional excipients; and (ii) a coating consisting essentially of a water-insoluble, water-permeable film-forming polymer, a plasticizer and a water-soluble polymer.

The invention thus provides a new drug controlled release composition under the form of a tablet, the core of which comprising the active ingredient. Also, the controlled release is obtained thanks to a semi-permeable release coating, free of (monomeric) pore-forming agent. The tablets of the invention exhibit specific dissolution profiles.

DETAILED DESCRIPTION OF THE INVENTION

The invention consists in a tablet comprising a core and a coating.

The core includes the active ingredient, and conventional excipients, notably a lubricant, and a binder and/or a filler, and optionally a glidant as well as other excipients.

Examples of lubricants include stearic acid, magnesium stearate, glyceryl behenate, stearyl behenate, talc, mineral oil (in PEG), sodium stearyl fumarate, etc.. Stearyl behenate is one preferred lubricant. Examples of binders include water-soluble polymer, such as modified starch, gelatin, polyvinylpyrrolidone, polyvinylalcohol (PVA), etc.. The preferred binder is polyvinylalcohol. Examples of fillers include lactose, microcristalline cellulose, etc, the latter being preferred. An example of glidant is silicon dioxide (Aerosil® of Degussa). A further pharmaceutical aid that can be used with advantage in the invention is fumaric acid. The above binders, lubricants, fillers, glidants, and any other excipient that may be present can further be found in the relevant literature, for example in the Handbook of Pharmaceutical Excipients. An acidifying or alkanizing agent can be present. The relative amounts of ingredients in the core are preferably as follows. The proportion of active ingredient in the core may vary between broad limits, as will recognize the skilled man. The proportion of lubricant and/or glidant, of binder, filler or any other excipients may also vary between broad limits, as will recognize the skilled man in the pharmaceutical field.

The active ingredient is preferably selected from the group consisting of oxybutynin hydrochloride, propranolol hydrochloride, buspiron hydrochloride, niacin, cetirizin hydrochloride, cerivastin sodium, metoprolol fumarate, and alendronate sodium.

The manufacturing process of the core can be as follows. The active ingredient and optionally other ingredients is first granulated with a binder, in a granulator, preferably but not necessarily a fluidized bed granulator. The binder is first dissolved or dispersed in a suitable solvent, preferably water. The solution or suspension of binder is then sprayed onto the drug in a granulator, e.g. fluidized bed granulator. For example, fluidized bed granulators manufactured by Glatt (Germany) or Aeromatic (Switzerland) can be used for this operation. An alternative process can be to use a conventional or high shear mixer to proceed granulation. If necessary, the drug can be mixed with a filler, prior to the granulation step. Granules once dried can be mixed with the other excipients, especially with the lubricant, but also with glidants and any other excipient suitable to improve processing. The mixture of granules (preferably with lubricant), and optionally glidant is pressed into tablets. Alternatively, the active ingredient and lubricant and/or glidant can be mixed in a granulator, e.g. a fluidized bed granulator, and heated to the melting point of the lubricant to form granules. This mixture can then be mixed with a suitable filler and compressed into tablets. Also, it is possible to mix the active ingredient and the lubricant in a granulator, e.g. a fluidized bed granulator, and then to press the resulting granules into tablets. Tablets can be obtained by standard techniques, e.g. on a (rotary) press (for example Manesty Betapress®) fitted with suitable punches. The resulting tablets are hereinafter referred as tablet cores.

These tablet cores are then coated with the semi-permeable coating designed to achieve a controlled release of metformin.

The coating comprises a water-insoluble, water-permeable film-forming polymer, together with a plasticizer and a water-soluble polymer.

The water-insoluble, water-permeable film-forming polymer can be a cellulose ether, such as ethylcellulose, a cellulose ester, such as cellulose acetate, etc. The preferred film-forming polymer is ethylcellulose (available from Dow Chemical under the trade name Ethocel®). The plasticizer can be an ester such as a citrate ester or dibutyl sebacate, an oil such as castor oil, a polyalkyleneglycol such as polyethyleneglycol of various MWs, a fatty acid such as stearic acid. The preferred plasticizer is stearic acid. The water-soluble polymer is preferably polyvinylpyrrolidone (PVP) or a cellulose ether such as hydroxypropylcellulose (HPC). Some other excipients can be used in the coating, as for example acrylic acid derivatives (available from Roehm Pharma under the trade name "Eudragit®"), pigments, etc.. The relative amounts of ingredients in the coating are preferably as follows. The proportion of water-insoluble, water-permeable polymer (e.g. ethylcellulose) in the coating may vary between 20 and 85% of the coating dry weight. The proportion of water-soluble polymer (e.g. polyvinylpyrrolidone or HPC) in the coating may vary between 10 and 75% of the coating dry weight. The proportion of plasticizer (e.g. stearic acid) in the coating may vary between 5 and 30% of the coating dry weight. The relative proportions of ingredients, notably the ratio water-insoluble, water-permeable film-forming polymer to water-soluble polymer, can be varied depending on the release profile to be obtained (where a more delayed release is generally obtained with a higher amount of water-insoluble, water-permeable film-forming polymer).

The coating process can be as follows. Ethylcellulose, stearic acid and polyvinylpyrrolidone or HPC are dissolved in a solvent such as ethanol. The resulting solution is sprayed onto the tablet cores, using a coating pan or a fluidized bed apparatus.

The weight ratio coating/tablet core is comprised e.g. between 1/50 and 5/10.

The tablet comprises an amount of active ingredient that can be from 0.1 to 1500 mg per tablet, depending on the specific active ingredient selected.

Surprisingly, it was discovered that the above formulation did not lead to any degradation of the active ingredient though no stabilizer was present in the formulation. Stability studies were conducted in oven, under the storage test conditions described in the US pharmacopoeia 23$^{rd}$ edition page 1961. Under these conditions no significant change in drug potency could be seen.

Surprisingly, it was also discovered that the above formulation did provide a controlled (sustained) release though no pore-forming agent was present in the coating.

The invention thus provides a controlled release tablet free of stabilizer and free of pore-forming agent, exhibiting a dissolution profile such that after 2 hours, from 5 to 40% of the active ingredient is released, after 4 hours, from 10 to 60% of the active ingredient is released, after 12 hours, from 50 to 98% of the active ingredient is released, after 24 hours, more than 80% of the active ingredient is released.

BEST MODES FORE CARRYING THE INVENTION

A preferred tablet composition comprises:
(i) a core comprising the active ingredient, optionally silicon dioxide, polyvinylpyrrolidone or polyvinylalcohol, glyceryl behenate or sodium stearyl fumarate and optionally lactose and optionally fumaric acid; and
(ii) a coating comprised of ethylcellulose, polyvinylpyrrolidone or hydroxypropylcellulose and stearic acid.

A preferred oxybutynin hydrochloride tablet composition comprises:
(i) a core comprising oxybutynin hydrochloride, silicon dioxide, polyvinylpyrrolidone, sodium stearyl fumarate, lactose and fumaric acid; and
(ii) a coating comprised of ethylcellulose, polyvinylpyrrolidone and stearic acid.

A preferred propranolol hydrochloride tablet composition comprises:
(i) a core comprising propranolol, silicon dioxide, polyvinylalcohol, and sodium stearyl fumarate and lactose; and
(ii) a coating comprised of ethylcellulose, polyvinylpyrrolidone or hydroxypropylcellulose and stearic acid.

A preferred buspiron hydrochloride tablet composition comprises:
(i) a core comprising buspiron hydrochloride, silicon dioxide, polyvinylpyrrolidone, glyceryl behenate and lactose; and
(ii) a coating comprised of ethylcellulose, hydroxypropylcellulose and stearic acid.

A preferred niacin tablet composition comprises:
(i) a core comprising niacin, silicon dioxide, polyvinylpyrrolidone, sodium stearyl fumarate; and
(ii) a coating comprised of ethylcellulose, polyvinylpyrrolidone and stearic acid.

A preferred cetirizin hydrochloride tablet composition comprises:
(i) a core comprising cetirizin hydrochloride, silicon dioxide, polyvinylalcohol, glyceryl behenate and lactose; and
(ii) a coating comprised of ethylcellulose, hydroxypropylcellulose and stearic acid.

A preferred cerivastin sodium tablet composition comprises:
(i) a core comprising cerivastin sodium, silicon dioxide, polyvinylpyrrolidone, glyceryl behenate and lactose; and
(ii) a coating comprised of ethylcellulose, polyvinylpyrrolidone and stearic acid.

A preferred metoprolol fumarate tablet composition comprises:
(i) a core comprising metoprolol fumarate, polyvinylpyrrolidone, glyceryl behenate; and
(ii) a coating comprised of ethylcellulose, hydroxypropylcellulose and stearic acid.

A preferred alendronate sodium tablet composition comprises:
(i) a core comprising alendronate sodium, polyvinylpyrrolidone, sodium stearyl fumarate and lactose; and
(ii) a coating comprised of ethylcellulose, polyvinylpyrrolidone and stearic acid.

EXAMPLES

The following examples illustrate the invention without limiting it, where the amounts are given per dosage form.

Example 1

Oxybutynin Hydrochloride

The following formulation is prepared.

| Ingredients | Amount (mg) |
| --- | --- |
| Oxybutynin hydrochloride | 15.00 |
| Polyvinylpyrrolidone | 15.00 |
| Silicon dioxide | 3.00 |
| Lactose | 100.00 |
| Fumaric acid | 30.00 |
| Sodium stearyl fumarate | 1.50 |
| Total (dry weight) | 164.50 |

Oxybutynin hydrochloride, fumaric acid and lactose are placed in a fluidized bed apparatus. An aqueous PVP solution (in 85 g of water) is sprayed to get granules. The apparatus is a Glatt GPCG1, operated with the following parameters.

| | |
| --- | --- |
| Air flow (m$^3$/h) | 100–110 m$^3$/h |
| Liquid flow (g/min) | 6–7 g/min |
| Inlet temperature | 65° C. |
| Spraying pressure | 2.8 bar |

The granules thus obtained are subsequently dried. Then they are passed through a sieve (1 mm mesh) and sodium stearyl fumarate is weighed, added and blended in a drum mixer (Turbula T2C, Bachoffen, Switzerland). The resulting mixture is pressed into tablets (7 mm diameter and 7 mm curvature) with average hardness being between 60 and 120N. These tablet cores are then coated with the following formulation.

| Ingredients | Amount (mg) |
|---|---|
| Tablet cores | 164.50 |
| Ethylcellulose (Ethocel) | 10.10 |
| Polyvinylpyrrolidone (Povidone) | 5.50 |
| Stearic acid | 2.40 |
| Total (dry weight) | 182.50 |

Ethocel, povidone and stearic acid are first dissolved in denatured alcohol (180 g). The coating solution is then sprayed onto the tablet cores in a coating pan (Vector LCDS), with the following spraying parameters:

| | |
|---|---|
| Air flow (m³/h) | 100–110 m³/h |
| Liquid flow (g/min) | 6–7 g/min |
| Inlet temperature | 65° C. |
| Spraying pressure | 2.8 bar |

Example 2
Propranolol Hydrochloride

According to the procedure given in example 1, the following formulation is prepared (water and alcohol will evaporate off during the process):

| Core composition. | |
|---|---|
| Ingredients | Amount (mg) |
| Propranolol hydrochloride | 120.00 |
| Polyvinylalcohol | 4.00 |
| Silicon dioxide | 2.00 |
| Lactose | 80.00 |
| Sodium stearyl fumarate | 2.00 |
| Water | 200.00 |
| Total (dry weight) | 208.00 |

| Coating composition. | |
|---|---|
| Ingredients | Amount (mg) |
| Ethylcellulose | 9.81 |
| Povidone | 3.53 |
| Stearic acid | 2.66 |
| alcohol | 188.00 |

Example 3
Buspiron Hydrochloride

According to the procedure given in example 1, the following formulation is prepared (water and alcohol will evaporate off during the process):

| Core composition. | |
|---|---|
| Ingredients | Amount (mg) |
| Buspiron hydrochloride | 15.00 |
| Polyvinylpyrrolidone | 7.00 |
| Silicon dioxide | 1.50 |

| Core composition. | |
|---|---|
| Ingredients | Amount (mg) |
| Lactose | 150.00 |
| Glyceryl behenate | 1.50 |
| Water | 100.00 |
| Total (dry weight) | 175.00 |

| Coating composition. | |
|---|---|
| Ingredients | Amount (mg) |
| Ethylcellulose | 10.00 |
| Hydroxypropylcellulose | 10.00 |
| Stearic acid | 2.00 |
| alcohol | 188.00 |

Example 4
Niacin

According to the procedure given in example 1, the following formulation is prepared (water and alcohol will evaporate off during the process):

| Core composition. | |
|---|---|
| Ingredients | Amount (mg) |
| Niacin | 1000.00 |
| Polyvinylpyrrolidone | 40.00 |
| Silicon dioxide | 10.00 |
| Sodium stearyl fumarate | 15.00 |
| Water | 400.00 |
| Total (dry weight) | 1065.00 |

| Coating composition. | |
|---|---|
| Ingredients | Amount (mg) |
| Ethylcellulose | 26.50 |
| Povidone | 9.55 |
| Stearic acid | 3.95 |
| alcohol | 550.00 |

Example 5
Cetirizin Hydrochloride

According to the procedure given in example 1, the following formulation is prepared (water and alcohol will evaporate off during the process):

| Core composition. | |
|---|---|
| Ingredients | Amount (mg) |
| Cetirizin hydrochloride | 15.00 |
| Polyvinylalcohol | 3.00 |
| Silicon dioxide | 1.50 |
| Lactose | 135.00 |
| Glyceryl behenate | 1.50 |

-continued

| Core composition. | |
|---|---|
| Ingredients | Amount (mg) |
| Water | 100.00 |
| Total (dry weight) | 156.00 |

| Coating composition. | |
|---|---|
| Ingredients | Amount (mg) |
| Ethylcellulose | 10.00 |
| Hydroxypropylcellulose | 5.00 |
| Stearic acid | 1.50 |
| alcohol | 250.00 |

Example 6

Cerivastin Sodium

According to the procedure given in example 1, the following formulation is prepared (water and alcohol will evaporate off during the process):

| Core composition. | |
|---|---|
| Ingredients | Amount (mg) |
| Cerivastin sodium | 0.5 |
| Polyvinylpyrrolidone | 7.50 |
| Silicon dioxide | 1.50 |
| Lactose | 150.00 |
| Glyceryl behenate | 1.50 |
| Water | 90.00 |
| Total (dry weight) | 164.00 |

| Coating composition. | |
|---|---|
| Ingredients | Amount (mg) |
| Ethylcellulose | 10.00 |
| Polyvinylpyrrolidone | 6.00 |
| Stearic acid | 1.60 |
| Alcohol | 160.00 |

Example 7

Metoprolol Fumarate

According to the procedure given in example 1, the following formulation is prepared (water and alcohol will evaporate off during the process):

| Core composition. | |
|---|---|
| Ingredients | Amount (mg) |
| Metoprolol fumarate | 200.00 |
| Polyvinylpyrrolidone | 10.00 |
| Glyceryl behenate | 2.00 |
| Water | 100.00 |
| Total (dry weight) | 212.00 |

| Coating composition. | |
|---|---|
| Ingredients | Amount (mg) |
| Ethylcellulose | 10.00 |
| Hydroxypropylcellulose | 5.00 |
| Stearic acid | 1.50 |
| Alcohol | 160.00 |

Example 8

Alendronate Sodium

According to the procedure given in example 1, the following formulation is prepared (water and alcohol will evaporate off during the process):

| Core composition. | |
|---|---|
| Ingredients | Amount (mg) |
| Alendronate sodium | 52.00 |
| Polyvinylpyrrolidone | 10.00 |
| Lactose | 100.00 |
| Sodium stearyl fumarate | 1.50 |
| Water | 100.00 |
| Total (dry weight) | 163.50 |

| Coating composition. | |
|---|---|
| Ingredients | Amount (mg) |
| Ethylcellulose | 10.00 |
| Polyvinylpyrrolidone | 5.00 |
| Stearic acid | 1.50 |
| Alcohol | 160.00 |

Stability Data

Storage conditions: conforms to USP 23 guideline (25° C. and 60% relative humidity and 40° C. and 75% relative humidity). The results show that the tablet compositions of the invention are stable.

Dissolution Profile

Dissolution conditions:

Medium: 1000 ml phosphate buffer pH 6.8.

Method: 75 rpm USP Apparatus I.

All tablet compositions show a release profile that is according to the ranges given in the table below:

| Time (hour) | Release rate (%) |
|---|---|
| 2 | 5–40 |
| 4 | 10–60 |
| 12 | 50–98 |
| 24 | >80 |

The invention is not limited to the specific embodiments described above but can be varied within broad limits by the skilled man.

What is claimed is:

1. A delayed release tablet comprising:

(i) a core comprising an active ingredient selected from the group consisting of oxybutynin hydrochloride, propranolol hydrochloride, buspiron hydrochloride, niacin, cetirizin hydrochloride, cerivastin sodium, metoprolol fumarate, and alendronate sodium, and conventional excipients; and (ii) a coating consisting essentially by weight, based on the coating weight, of 20 to 85% of a water-insoluble, water-permeable film-forming polymer, of 10 to 75% of a water-soluble polymer and 5 to 30% of a plasticizer, exhibiting a dissolution profile such that after 2 hours, from 5 to 40% of the active ingredient is released, after 4 hours, from 10 to 60% of the active ingredient is released, after 12 hours, from 50 to 98% of the active ingredient is released, after 24 hours, more than 80% of the active ingredient is released.

2. The tablet of claim 1, where the water-insoluble, water-permeable film-forming polymer is ethylcellulose.

3. The tablet of claim 1, where the water-soluble polymer is polyvinylpyrrolidone.

4. The tablet of claim 1, where the plasticizer is stearic acid.

5. The tablet of claim 1, where the water-insoluble, water-permeable film-forming polymer is ethylcellulose, the water-soluble polymer is polyvinylpyrrolidone and the plasticizer is stearic acid.

6. The tablet of claim 1, being an oxybutynin hydrochloride tablet composition comprising:
    (i) a core comprising oxybutynin hydrochloride, silicon dioxide, polyvinylpyrrolidone, sodium stearyl fumarate, lactose and fumaric acid; and
    (ii) a coating comprised of ethylcellulose, polyvinylpyrrolidone and stearic acid.

7. The tablet of claim 1, being a propranolol hydrochloride tablet composition comprising:
    (i) a core comprising propranolol hydrochloride, silicon dioxide, polyvinylalcohol, and sodium stearyl fumarate and lactose; and
    (ii) a coating comprised of ethylcellulose, polyvinylpyrrolidone or hydroxypropylcellulose and stearic acid.

8. The tablet of claim 1, being a buspiron hydrochloride tablet composition comprising:

(i) a core comprising buspiron hydrochloride, silicon dioxide, polyvinylpyrrolidone, glyceryl behenate and lactose; and (ii) a coating comprised of ethylcellulose, hydroxypropylcellulose and stearic acid.

9. The tablet of claim 1, being a niacin tablet composition comprising:
    (i) a core comprising niacin, silicon dioxide, polyvinylpyrrolidone, sodium stearyl fumarate; and
    (ii) a coating comprised of ethylcellulose, polyvinylpyrrolidone and stearic acid.

10. The tablet of claim 1, being a cetirizin hydrochloride tablet composition comprising:
    (i) a core comprising cetirizin hydrochloride, silicon dioxide, polyvinylalcohol, glyceryl behenate and lactose; and
    (ii) a coating comprised of ethylcellulose, hydroxypropylcellulose and stearic acid.

11. The tablet of claim 1, being a cerivastin sodium tablet composition comprising:
    (i) a core comprising cerivastin sodium, silicon dioxide, polyvinylpyrrolidone, glyceryl behenate and lactose; and
    (ii) a coating comprised of ethylcellulose, polyvinylpyrrolidone and stearic acid.

12. The tablet of claim 1, being a metoprolol fumarate tablet composition comprising:
    (i) a core comprising metoprolol fumarate, polyvinylpyrrolidone, glyceryl behenate; and
    (ii) a coating comprised of ethylcellulose, hydroxypropylcellulose and stearic acid.

13. (Amended) The tablet of claim 1, being an alendronate sodium tablet composition comprising:
    (i) a core comprising alendronate sodium, polyvinylpyrrolidone, sodium stearyl fumarate and lactose; and
    (ii) a coating comprised of ethylcellulose, polyvinylpyrrolidone and stearic acid.

* * * * *